United States Patent
Villongco et al.

(10) Patent No.: US 10,556,113 B2
(45) Date of Patent: Feb. 11, 2020

(54) PATIENT-SPECIFIC MODELING OF VENTRICULAR ACTIVATION PATTERN USING SURFACE ECG-DERIVED VECTORCARDIOGRAM IN BUNDLE BRANCH BLOCK

(71) Applicant: The Regents Of The University Of California, Oakland, CA (US)

(72) Inventors: Christopher T. Villongco, San Diego, CA (US); Jeffrey H. Omens, San Diego, CA (US); Andrew D. McCulloch, San Diego, CA (US); David E. Krummen, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/320,644

(22) PCT Filed: Jun. 19, 2015

(86) PCT No.: PCT/US2015/036788
§ 371 (c)(1),
(2) Date: Dec. 20, 2016

(87) PCT Pub. No.: WO2015/196140
PCT Pub. Date: Dec. 23, 2015

(65) Prior Publication Data
US 2017/0209698 A1    Jul. 27, 2017

Related U.S. Application Data

(60) Provisional application No. 62/015,273, filed on Jun. 20, 2014, provisional application No. 62/152,363, filed on Apr. 24, 2015.

(51) Int. Cl.
*A61B 5/00* (2006.01)
*A61N 1/362* (2006.01)
(Continued)

(52) U.S. Cl.
CPC ........ *A61N 1/3627* (2013.01); *A61B 5/04011* (2013.01); *A61B 5/055* (2013.01);
(Continued)

(58) Field of Classification Search
CPC ............... A61B 5/055; A61B 5/04011; A61B 2576/023; A61B 6/032; A61N 1/3627
See application file for complete search history.

(56) References Cited

U.S. PATENT DOCUMENTS 5,273,038 A    12/1993 Beavin
6,501,979 B1    12/2002 Manning et al.
(Continued)

OTHER PUBLICATIONS

Aguado-Sierra, J., et. al. "Patient-specific modeling of dyssynchronous heart failure: a case study." *Progress in Biophysics and Molecular Biology*, vol. 107 No. 1, 2011, pp. 147-155.
(Continued)

*Primary Examiner* — Michael J D Abreu
(74) *Attorney, Agent, or Firm* — Mintz Levin Cohn Ferris Glovsky and Popeo, P.C.

(57) ABSTRACT

In some example embodiments, there may be provided a method. The method may include receiving three-dimensional image data representative of a heart; receiving electrical data representative of an electrophysiology of the heart; and generating, based on the received three-dimensional image data and the received electrical data, a computational model of the heart. Related systems and articles of manufacture may also be provided.

17 Claims, 7 Drawing Sheets

(51) Int. Cl.
| | |
|---|---|
| A61B 5/055 | (2006.01) |
| A61B 6/03 | (2006.01) |
| A61B 6/00 | (2006.01) |
| A61B 5/04 | (2006.01) |
| G16H 50/50 | (2018.01) |
| G01R 33/56 | (2006.01) |

(52) U.S. Cl.
CPC .............. *A61B 6/032* (2013.01); *A61B 6/037* (2013.01); *A61B 6/5247* (2013.01); *G16H 50/50* (2018.01); *A61B 2576/023* (2013.01); *G01R 33/5608* (2013.01)

(56) References Cited

U.S. PATENT DOCUMENTS

| | | | | |
|---|---|---|---|---|
| 7,010,347 | B2* | 3/2006 | Schecter | A61N 1/3627 607/17 |
| 2011/0251504 | A1* | 10/2011 | Tereshchenko | A61B 5/04011 600/512 |
| 2012/0035459 | A1 | 2/2012 | Revishvili et al. | |
| 2012/0283587 | A1 | 11/2012 | Gosh et al. | |
| 2014/0323882 | A1* | 10/2014 | Ghosh | A61N 1/3686 600/483 |

OTHER PUBLICATIONS

Alexander, D. C., et. al. "Spatial Transformations of Diffusion Tensor Magnetic Resonance Images." *IEEE Transactions on Medical Imaging*, vol. 20 No. 11, 2001, pp. 1131-1139.
Aronszajn, N. "Theory of reproducing kernels." *Transactions of the American Mathematical Society*, vol. 68, 1950, pp. 337-404.
Arsigny, V., et. al. "Log-Euclidean metrics for fast and simple calculus on diffusion tensors." *Magnetic Resonance in Medicine: Official Journal of the Society of Magnetic Resonance in Medicine / Society of Magnetic Resonance in Medicine*, vol. 56 No. 2, 2006, pp. 411-421.
Auricchio, A., et. al. "Characterization of left ventricular activation in patients with heart failure and left bundle-branch block." *Circulation*, vol. 109, No. 9, 2004, pp. 1133-1139.
Berger, T., et. al."Single-beat noninvasive imaging of cardiac electrophysiology of ventricular pre-excitation." *Journal of the American College of Cardiology*, vol. 48, No. 10, 2006, pp. 2045-2052.
Burger, H. C., and J.B. Van Milaan. "Heart-Vector and Leads." *British Heart Journal*, vol. 8, No. 3, 1946, pp. 157-161.
Cao, Y., et. al. "Large deformation diffeomorphic metric mapping of vector fields." *Medical Imaging, IEEE Transactions*, vol. 24, No. 9, 2005, pp. 1216-1230.
Cluitmans, M. J. M., et. al. "Inverse Reconstruction of Epicardial Potentials Improve by Vectorcardiography and Realistic Potentials." *Computing in Cardiology*, vol. 40, 2013, pp. 369-372.
Daubert, J.-C., et. al. "2012 EHRA/HRS expert consensus statement on cardiac resynchronization therapy in heart failure: implant and follow-up recommendations and management." *Heart Rhythm: The Official Journal of the Heart Rhythm Society*,vol. 9 No. 9, 2012, pp. 1524-1576.
De Vito, E., et. al. "Adaptive kernel methods using the balancing principle." *Foundations of Computational Mathematics*, vol. 10, No. 4, 2010, pp. 455-479.
De Vito, E., et. al. "Learning from examples as an inverse problem." *Journal of Machine Learning Research*, vol. 6, 2005, pp. 883-904.
Dossel, O., et. al. "Imaging of bioelectric sources in the heart using a cellular automaton model." *Conference Proceedings: Annual International Conference of the IEEE Engineering in Medicine and Biology Society. IEEE Engineering in Medicine and Biology Society. Conference*, 2005, pp. 1067-1070.
Edenbrandt, L., and O. Pahlm. "Vectorcardiogram synthesized from a 12-lead ECG: superiority of the inverse Dower matrix." *Journal of Electrocardiology*, vol. 21, No. 4, 1988, pp. 361-367.
Engl, H., et. al. "Regularization of Inverse Problems." *Mathematics and Its Application*, vol. 375, 1996.
Fillard, P., et. al.(2007). "Clinical DT-MRI estimation, smoothing, and fiber tracking with log-Euclidean metrics." *IEEE Transactions on Medical Imaging*, vol. 26, No. 11, 2007, pp. 1472-1482.
Gold, M. R., et. al. "The relationship between ventricular electrical delay and left ventricular remodelling with cardiac resynchronization therapy." *European Heart Journal*, vol. 32, No. 20, 2011, pp. 2516-2524.
Golub, G. H., and C. Reinsch,. "Singular Value Decomposition and Least Squares Solutions." *Numerische Mathematik*, vol. 14, 1970, pp. 403-420.
Gonzales, M. J., et. al. "A three-dimensional finite element model of human atrial anatomy: new methods for cubic Hermite meshes with extraordinary vertices." *Medical Image Analysis*,vol. 17 No. 5, 2013, pp. 525-537.
Greensite, F., and G.Huiskamp. "An improved method for estimating epicardial potentials from the body surface." *IEEE Transactions on Bio-Medical Engineering*, vol. 45, No. 1, 1998, pp. 98-104.
Guillem, M. S., et. al. "Derivation of orthogonal leads from the 12-lead ECG. Accuracy of a single transform for the derivation of atrial and ventricular waves." *In Computers in Cardiology*, 2006, pp. 249-252.
Han, C., et. al. "Noninvasive reconstruction of the three-dimensional ventricular activation sequence during pacing and ventricular tachycardia in the rabbit heart." *Conference Proceedings: Annual International Conference of the IEEE Engineering in Medicine and Biology Society*,2011, pp. 1684-1687.
Han, C., et. al. "Noninvasive reconstruction of the three-dimensional ventricular activation sequence during pacing and ventricular tachycardia in the canine heart." *American Journal of Physiology. Heart and Circulatory Physiology*, vol. 302, No. 1, 2012, pp. H244-H252.
He, B., et. al. "Noninvasive three-dimensional activation time imaging of ventricular excitation by means of a heart-excitation model." *Physics in Medicine and Biology*, vol. 47, No. 22, 2002, pp. 4063-4078.
Kimeldorf, G., and G. Wahba. "Some results on Tchebycheffian spline functions." *Journal of Mathematical Analysis and Applications*, vol. 33, 1971, pp. 82-95.
Kindermann, S., and A.Neubauer. "On the convergence of the quasi-optimality criterion for (iterated) Tikhonov regularization." *Inverse Problems and Imaging*, vol. 2, No. 2, 2008, pp. 291-299.
Kors, J. A., et. al. "Reconstruction of the Frank vectorcardiogram from standard electrocardiographic leads: diagnostic comparison of different methods." *European Heart Journal*, vol. 11, No. 12, 1990, pp. 1083-1092.
Krishnamurthy, A., Villongco, C. T., Chuang, J., Frank, L. R., Nigam, V., Belezzuoli, E., . . . Kerckhoffs, R. C. P. (2012). Patient-Specific Models of Cardiac Biomechanics. Journal of Computational Physics, 244, 4-21.
Li, G., and B. He. "Localization of the site of origin of cardiac activation by means of a heart-model-based electrocardiographic imaging approach." *IEEE Transactions on Bio-Medical Engineering*, vol. 48, No. 6, 2001, pp. 660-669.
Lin, T., et. al. "Implant electrical characteristics predict response to cardiac resynchronization therapy." *World Journal of Cardiovascular Diseases*, 2014.
Liu, C., et. al. "Estimation of global ventricular activation sequences by noninvasive 3-dimensional electrical imaging: validation studies in a swine model during pacing." *Journal of Cardiovasc Electrophysiol*, vol. 19, No. 5, 2009, pp. 535-540.
Messinger-Rapport, B. J., and Y. Rudy. "Regularization of the inverse Problem in Electrocardiography: A Model Study." *Mathematical Biosciences*, vol. 89, 1998, pp. 79-118.
Micchelli, C. A., and M. Pontil. "Learning the kernel function via regularization." *Journal of Machine Learning Research*, vol. 6, 2005, pp. 1099-1125.
Naumova, V., et. al. "Extrapolation in variable RKHSs with application to the blood glucose reading." *Inverse Problems*, vol. 27, No. 7, 2011, pp. 1-13.

(56) References Cited

OTHER PUBLICATIONS

Naumova, V., et. al. "A meta-learning approach to the regularized learning—case study: Blood glucose prediction." *Neural Networks*, vol. 33, 2012, pp. 181-193.
Oster, H. S., and Y. Rudy. "The use of temporal information in the regularization of the inverse problem of electrocardiography." *IEEE Transactions on Bio-Medical Engineering*, vol. 39, No. 1, 1992, pp. 65-75.
Pfeifer, B., et. al. "Patient-specific volume conductor modeling for non-invasive imaging of cardiac electrophysiology." *The Open Medical Informatics Journal*, vol. 2, 2008, pp. 32-41.
Ploux, S., et. al. "Noninvasive electrocardiographic mapping to improve patient selection for cardiac resynchronization therapy: beyond QRS duration and left bundle branch block morphology." *Journal of the American College of Cardiology*, vol. 61, No. 24, 2013, pp. 2435-2443.
Ramanathan, C., et. al. "Noninvasive electrocardiographic imaging for cardiac electrophysiology and arrhythmia." *Nature Medicine*, vol. 10, No. 4, 2004, pp. 422-428.
Ramanathan, C., et. al. "Noninvasive Electrocardiographic Imaging (ECGI): Application of the Generalized Minimal Residual (GMRes) Method." *Annals of Biomedical Engineering*, vol. 31, No. 8, 2003, pp. 981-994.
Rodriguez, L.-M., et. al. "Variable patterns of septal activation in patients with left bundle branch block and heart failure." *Journal of Cardiovascular Electrophysiology*, vol. 14, No. 2, 2003, pp. 135-141.
Rotter, M., et. al. "Reduction of fluoroscopy exposure and procedure duration during ablation of atrial fibrillation using a novel anatomical navigation system." *European Heart Journal*, vol. 26, No. 14, 2005, pp. 1415-1421.
Rudy, Y. "Noninvasive electrocardiographic imaging of arrhythmogenic substrates in humans." *Circulation Research*, vol. 112, No. 5, 2013, pp. 863-874.
Schreck, D. M.,et. al. "Statistical methodology: VI. Mathematical modeling of the electrocardiogram using factor analysis." *Academic Emergency Medicine*, vol. 5, No. 9, 1998, pp. 929-934.
Singh, J. P., et. al. "Left ventricular lead electrical delay predicts response to cardiac resynchronization therapy." *Heart Rhythm*, vol. 3, No. 11, 2006, pp. 1285-1292.
Strauss, D. G., et. al. "Defining left bundle branch block in the era of cardiac resynchronization therapy." *The American Journal of Cardiology*, vol. 107, No. 6, 2011, pp. 927-934.
Sweeney, M. O., et. al. "Analysis of ventricular activation using surface electrocardiography to predict left ventricular reverse volumetric remodeling during cardiac resynchronization therapy." *Circulation*, vol. 121, No. 5, 2010, pp. 626-634.
Ten Tusscher,et. al. "Alternans and spiral breakup in a human ventricular tissue model. American Journal of Physiology." *Heart and Circulatory Physiology*, vol. 291,2006, pp. H1088-H1100.
Tikhonov, A. N., et al. *Solutions of ill-posed problems*. Winston, (p. 258), 1997.
Tikhonov, A. N., amd V. B. Glasko. "Use of the regularization methods in non-linear problems." *USSR Computational Mathematics and Mathematical Physics*, vol. 5, 1965.
Vadakkumpadan, F., et. al. "Image-based estimation of ventricular fiber orientations for personalized modeling of cardiac electrophysiology." *Medical Imaging, IEEE Transactions*, vol. 31, No. 5, 2012, pp. 1051-1060.
Van der Graaf, A. W. M., et. al. "Noninvasive imaging of cardiac excitation: current status and future perspective. Annals of Noninvasive Electrocardiology." *The Official Journal of the International Society for Holter and Noninvasive Electrocardiology, Inc*, vol. 19, No. 2, 2014, pp. 105-113.
Van Deursen, C. J., et. al. "Vectorcardiography as a tool for easy optimization of cardiac resynchronization therapy in canine left bundle branch block hearts." *Circulation: Arrhythmia and Electrophysiology*, vol. 5, No. 3, 2012, pp. 544-552.
Vaquero, M., et. al. "Cardiac Fibrillation: From Ion Channels to Rotors in the Human Heart." *Heart Rhythm: The Official Journal of the Heart Rhythm Society*, vol. 5, No. 6, 2008, pp. 872-879.
Varma, N., et. al. "Electrocardiographic imaging of patients with heart failure with left bundle branch block and response to cardiac resynchronization therapy." *Journal of Electrocardiology*, vol. 40,2007, pp. S174-S178.
Villongco, C. T., et. al. "Patient-specific modeling of ventricular activation pattern using surface ecg-derived vectorcardiogram in bundle branch block." *Progress in Biophysics and Molecular Biology*, vol. 115, No. 2, 2014, pp. 305-313.
Wang, Y., et. al. "Noninvasive electroanatomic mapping of human ventricular arrhythmias with electrocardiographic imaging." *Science Translational Medicine*, vol. 3, No. 98, 2011, pp. 98ra84.
Wittkampf, F. H., et. al. "LocaLisa new technique for real-time 3-dimensional localization of regular intracardiac electrodes." *Circulation*, vol. 99, No. 10, 1999, pp. 1312-1317.
Yamashita, Y. "Theoretical studies on the inverse problem in electrocardiography and the uniqueness of the solution." *Biomedical Engineering, IEEE Transactions*, vol. 11, 1982, pp. 719-725.
Yushkevich, P. A., et. al. "User-guided 3D active contour segmentation of anatomical structures: significantly improved efficiency and reliability." *NeuroImage*, vol. 31, No. 3, 2006, pp. 1116-1128.
Zhang, X., et. al. "Noninvasive three-dimensional electrocardiographic imaging of ventricular activation sequence." *AJP-Heart Circulatory Physiology*, vol. 289, 2005, pp. 2724-2732.
Cortez, Daniel L., and Todd T. Schlegel. "When deriving the spatial QRS-T angle from the 12-lead electrocardiogram, which transform is more Frank: regression or inverse Dower?." *Journal of Electrocardiology* 43.4 (2010): 302-309.
Gulrajani, Ramesh M. "The forward and inverse problems of electrocardiography." *IEEE Engineering in Medicine and Biology Magazine* 17.5 (1998): 84-101.
Messnarz, Bernd, et al., "A new spatiotemporal regularization approach for reconstruction of cardiac transmembrane potential patterns." *IEEE transactions on Biomedical Engineering* 51.2 (2004): 273-281.

\* cited by examiner

DT-MR reconstruction

Mesh registration

Host fibre architecture

Mapped fibre architecture

Sesta-MIBI perfusion map

Infarction field

Human myocyte membrane potential

Monodomain reaction diffusion

PATIENT-SPECIFIC MODELING OF VENTRICULAR ACTIVATION PATTERN USING SURFACE ECG-DERIVED VECTORCARDIOGRAM IN BUNDLE BRANCH BLOCK

CROSS REFERENCE TO RELATED APPLICATIONS

This application is a national-phase entry of Patent Cooperation Treaty Application No. PCT/US2015/036788, filed Jun. 19, 2015, entitled "PATIENT-SPECIFIC MODELING OF VENTRICULAR ACTIVATION PATTERN USING SURFACE EGG-DERIVED VECTORCARDIOGRAM IN BUNDLE BRANCH BLOCK," and claims priority to U.S. Provisional Patent Application 62/015,273 filed Jun. 20, 2014, entitled "PATIENT-SPECIFIC MODELING OF VENTRICULAR ACTIVATION PATTERN USING SURFACE ECG-DERIVED VECTORCARDIOGRAM IN BUNDLE BRANCH BLOCK" and U.S. Provisional Patent Application 62/152,363 filed Apr. 24, 2015, entitled "PATIENT-SPECIFIC MODELING OF VENTRICULAR ACTIVATION PATTERN USING SURFACE ECG-DERIVED VECTORCARDIOGRAM IN BUNDLE BRANCH BLOCK," the contents of which are hereby incorporated by reference in their entirety.

STATEMENT OF GOVERNMENT SPONSORED SUPPORT

This invention was made with government support under HL096544 awarded by the National Institutes of Health. The government has certain rights in the invention.

TECHNICAL FIELD

The subject matter disclosed herein relates to determining a computational model of a human heart and associated methods and systems related to that computational model.

BACKGROUND

The sequence of electrical excitation in the ventricles of the heart may be an important indicator of cardiac health and disease. Intrinsic cardiac electrical conduction disorders, such as bundle branch block (BBB), may be detrimental to normal mechanical synchrony and pump efficiency. In device-based treatments for heart failure (HF) such as cardiac resynchronization therapy (CRT), the appropriate therapeutic parameters and therapeutic response may be dependent on the patient-specific baseline electrophysiological substrate.

SUMMARY

Methods and apparatus, including computer program products, are provided for computational modeling of the heart.

In some example embodiments, there is provided a method. The method may include receiving three-dimensional image data representative of a heart; receiving electrical data representative of an electrophysiology of the heart; and generating, based on the received three-dimensional image data and the received electrical data, a computational model of the heart.

In some example embodiments, one of more variations may be made as well as described in the detailed description below and/or as described in the following features. The electrical data may include time varying electrocardiogram data. The three-dimensional image data may include at least one of an echocardiograph, a computed tomograph, a myocardial perfusion scan, or a magnetic resonance image set. The generating may further include generating a finite element mesh of the heart including the left and right ventricles and aligning a location associated with the received electrical data to the same location in the generated finite element mesh. A simulated heart vector may be determined from the generated computational model. The simulated heart vector may predict a vectorcardiogram of a patient. The simulated heart vector may be adjusted based on a comparison of the simulated heart vector to the vectorcardiogram. The vectorcardiogram may be estimated using a 12-lead electrocardiogram obtained from the patient. The comparison may be based on optimizing an objective function to determine model parameters specific to the patient's electrophysiology. One or more parameters or variables indicative of patient responsiveness to cardiac resynchronization therapy may be determined from the computational model of the heart. The one or more parameters may include an indication of dyssynchrony. The one or more parameters may include at least one of a dyssynchrony metric, an origin of the electrical activation, a conductivity of a myocardial tissue, or a speed at which the activation traverses the myocardium. The dyssynchrony metric may include at least one of a first total activation duration in an entire left ventricle, a second total activation duration between an earliest activation time in a septum and a latest activation in the entire left ventricle, a first delay between mean activation times in the septum and a portion of a left ventricular lateral wall, a first difference in total activation times between the septum and a portion of a right ventricular wall, a second delay between the earliest activation times in the septum and a right ventricle, a second delay between the earliest activation times in the entire left ventricle and the right ventricle, a second difference in total activation times between left ventricular and right ventricular walls, a third delay between earliest activation times in left and right ventricles, a second difference in total activation times between a left ventricular lateral wall and a right ventricular wall, and/or a fourth delay between earliest activation times in the left ventricular lateral wall and the right ventricle. A treatment configuration for the cardiac resynchronization therapy may be adjusted based on the one or more parameters. The adjusted treatment parameters may include cardiac resynchronization therapy lead placement and/or interventricular stimulation delay. A user interface may be generated for presentation on a display, wherein the user interface includes a representation of the generated computational model of the heart and one or more parameters indicative of patient responsiveness to cardiac resynchronization therapy. The computational model may include a four dimensional model of the heart.

DESCRIPTION OF THE DRAWINGS

The accompanying drawings, which are incorporated in and constitute a part of this specification, show certain aspects of the subject matter disclosed herein and, together with the description, help explain some of the principles associated with the subject matter disclosed herein. In the drawings.

DETAILED DESCRIPTION

There are disclosed herein systems, methods, and articles of manufacture for generating patient-specific computational models that can be used to diagnose certain cardiac diseases and to plan certain cardiac therapy.

In some example embodiments, the patient-specific model may include the 3D structural anatomy of a patient's heart and at least an additional dimension representing the dynamics of the heart, resulting in a 4D model. The $4^{th}$ dimension may thus correspond to time, in accordance with some example embodiments. The dynamics of the heart result from electrical activation spreading throughout the myocardial tissue, and have associated trajectories (identified from electrocardiogram, ECG, data of the patient and/or vectorcardiogram, VCG, data of the patient and/or the like). Although some of the examples described herein refer to the 4D model of the heart, the model may be of a certain portion of the heart as well, such as the right ventricle and left ventricle regions of the heart. Moreover, although some of the examples described herein refer to a 4D model, the model may be of other dimensions as well, and may for example be a function of additional independent variables.

In some example embodiments, the patient-specific model, also referred to herein as the 4D model, may be used to determine a simulated heart vector. From this simulated heart vector, a dyssynchrony metric and/or other parameter(s) may be determined. The dyssynchrony metric or other parameter(s) may be used to diagnose the severity of certain cardiac disorders including diseases and/or to plan certain cardiac therapy and/or to assess the efficacy of such therapy.

In some example embodiments, the patient-specific computational 4D model may be used to configure parameters of a cardiac treatment, such as cardiac resynchronization therapy (CRT). For example, the dyssynchrony metric and/or other parameter(s) determined from the patient-specific 4D model may be used to configure the cardiac treatment including cardiac resynchronization therapy lead placement and/or varying cardiac resynchronization therapy pacing parameters, such as interventricular (V-V) stimulation delay.

In some example embodiments, the patient-specific 4D model may be specific to a given patient, although the patient-specific 4D model may be generalized as well in order to simulate a plurality or population of patients. Moreover, the 4D model may be generated based on patient-specific data, simulated data, and/or data that is machine-learned through for example a neural network or other machine learning technique. And, the 4D model itself (or one or more of its output variables or solutions) may be modeled using machine learning.

Figure 1:
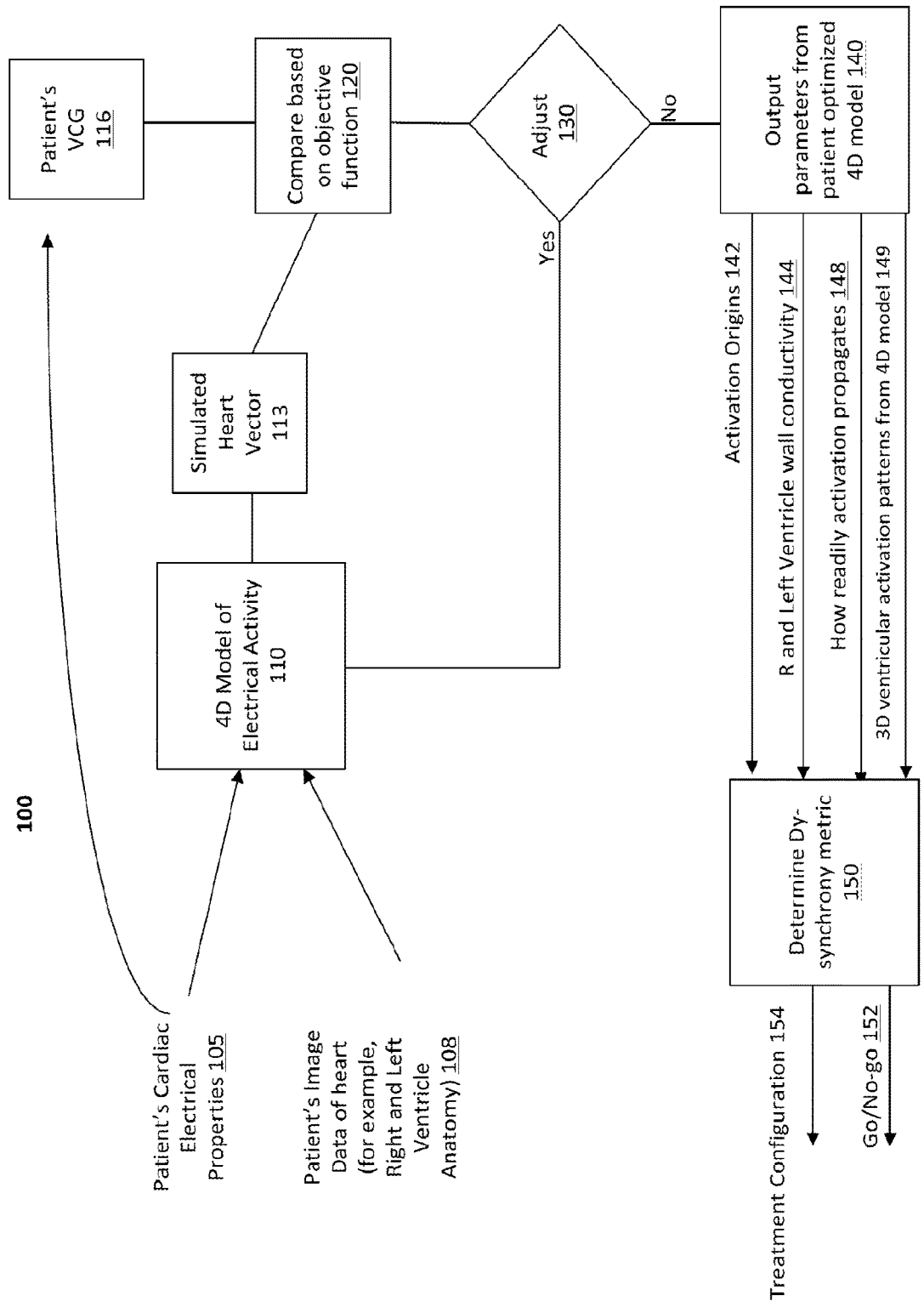
FIG. 1 depicts an example process for determining a computational model of a patient's heart, in accordance with some example embodiments.

FIG. 1 depicts an example of a process 100 for generating a computational model, such as a 4D model, of the human heart, in accordance with some example embodiments. The 4D computational model may be used to diagnose and treat certain cardiac conditions, such as those related to abnormal ventricular activation sequence in heart failure. Heart failure is a complex disease state that may have changes in ventricular shape, fiber orientation, ion channel expression remodeling, and/or other conditions/changes as well. The computational heart model, as noted, may be patient-specific in the sense that the data used to generate the 4D model and the parameters/metrics used in connection with the 4D model may be specific to a given patient taking the above-noted conditions/changes into account, although as noted above the 4D model may be generalized as well.

At 105, measurements of a patient's cardiac electrical properties may be received. For example, a data processor, such as a computer and the like, may receive a given patient's electrocardiogram (ECG) data. The electrocardiogram data may be obtained from a 12-lead ECG that records the continuous, dynamic signals of cardiac electrical function from multiple body locations.

At 108, imaging data of a patient's heart including right and left ventricles may be received. For example, the data processor may receive image data that includes heart images (or portions thereof, such as the right and left ventricles) obtained from clinical cardiac computed tomography (CT), 2D or 3D echocardiography, myocardial perfusion scans, magnetic resonance images (MRI), and/or other images of a heart and/or portions thereof.

At 110, a 4D patient specific computational model of a patient's electrical activity may be generated. For example, the data processor may generate a 4D model based on the 3D data received at 108 and the added dynamics from the electrical activity from the data received at 105. The 4D computational model may provide a 3D representation of the morphology and anatomy of the heart (or portions thereof, such as the right and left ventricles) over time, and further provide the time-varying electrical dynamics of the heart (or portions thereof), such as time-varying ECG data. The electrical dynamics may include the activation patterns and the electrical trajectories of the activations through the myocardium, and the electrical dynamics may include patterns (for example, sequences) of electrical repolarization/recovery. The model may also include additional aspects, such as the regional distribution of perfusion or infarction, which may be measured in the individual patient.

For example, the electrical data, such as the time-varying ECG data, received at 105 may be combined with the imaging data received at 108 to generate the 4D patient specific model 110. From this 4D patient specific model, a simulated heart vector 113 may be generated by the data processor (as described further below at 113). This simulated heart vector may be used as a predictor (or estimate) of a vector cardiogram (VCG) or heart dipole. The VCG generally indicates cardiac electrical activities along three orthogonal planes of the body, frontal, transverse, and sagittal. As such, the simulated heart vector disclosed herein may, in some example embodiments, provide an estimate (or simulation) of the VCG overlaid on the morphology of the heart.

In some example embodiments, the 4D model 110 may include ECG data overlaid and registered on the 3D biventricular geometry of the patient's heart (for example, generated using finite element meshes), the human fiber architecture of the heart, and/or region(s) of heterogeneous conductivities caused by the presence of myocardial ischemia, infarction(s), and/or anatomic (and/or functional) electrical conduction defects, such as partial and/or complete bundle branch block.

Figure 2A:
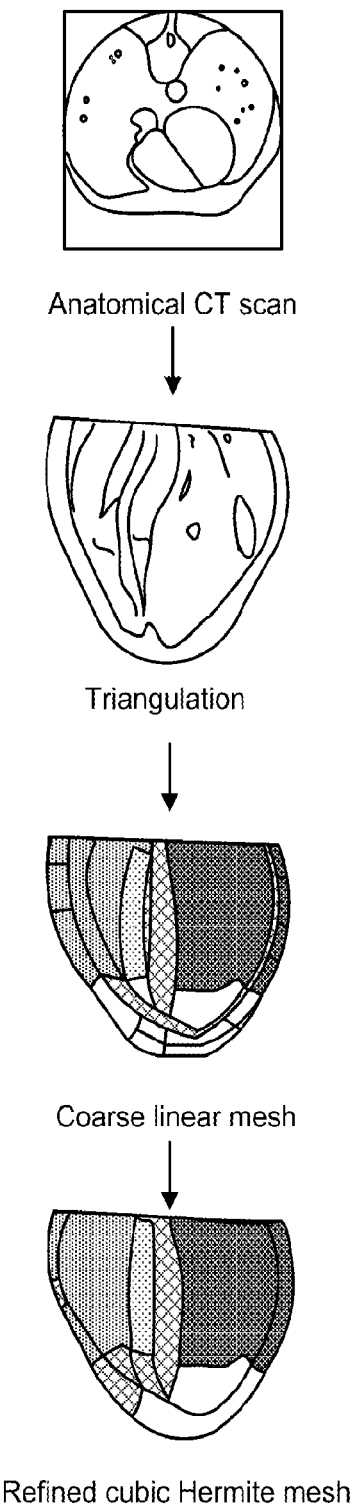
FIGS. 2A-D depict examples of data used when generating the computational model, in accordance with some example embodiments.

The patient-specific finite element meshes of the heart (which may include its ventricular anatomy) may be generated, as noted, from the received image data 108, such as the clinical CT, perfusion images, MRI and/or other types of image data. FIG. 2A depicts an example CT scan and how that CT scan is aligned and spatially discretized and further processed to generate a finite element mesh of the heart or walls or part thereof.

Figure 2B:
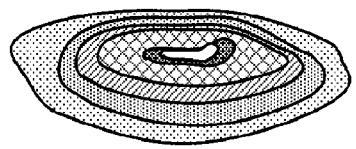
Figure 2B:
Figure 2B:
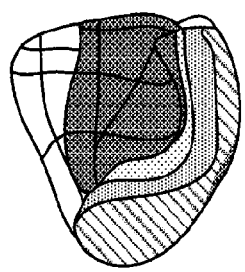
Figure 2B:
Figure 2B:
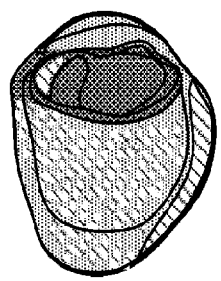
Figure 2B:
Figure 2B:
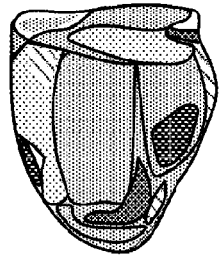

The 4D model may also include, as noted, the heart's fiber architecture. The heart's fiber architecture may be estimated empirically using for example a log-Euclidean interpolation framework for registering DT-MR measurements to the anatomical models. FIG. 2B depicts an example of the mapped fiber architecture determine from DT-MR measurements in for example a cadaveric heart, although the DT-MR measurements and the like can use data from non-cadaveric heart(s) as well. The reconstructed diffusion tensors may be fitted as a field of log-transformed components in a corresponding anatomical mesh to interpolate local fiber, sheet, and sheet-normal axes. The fiber orientations in the resulting model may be mapped to a patient via large-deformation diffeomorphic mapping and reoriented based on the 3D deformation gradients between the template and target patient ventricular geometries to account for the effect of ventricular shape differences on fiber orientation. The resulting fiber-sheet model forms the local basis of transversely isotropic or orthotropic ventricular electrical conductivity (which may have a fiber-sheet anisotropy ratio of about 7:1 for example).

Figure 2C:
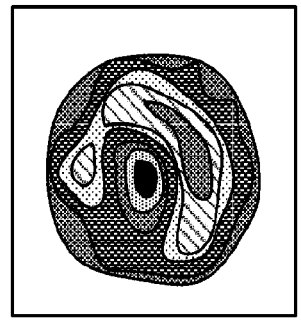
Figure 2C:
Figure 2C:
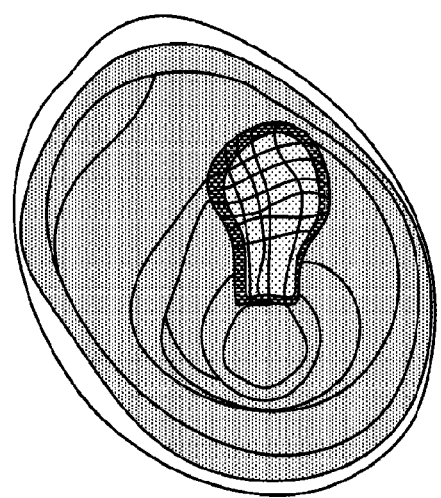

The 4D model may also include regions of myocardial ischemia, infarction, and/or other like regions. When that is the case, myocardial ischemic or infarcted regions may be identified from, for example, perfusion images and/or sestamibi perfusion images obtained during stress and rest as shown in FIG. 2C. The myocardial ischemia or infarction boundary regions may be demarcated on the generated anatomical meshes of the heart as shown in FIG. 2C. For example, a patient may have a posteroseptal infarction, and may have an inferior infarction. These regions may be registered in the 4D model as a binary field of normal and infarcted tissue.

Figure 2D:
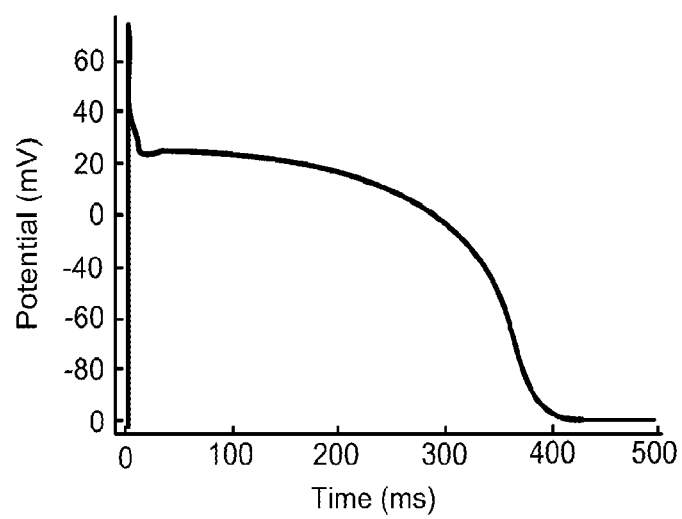
Figure 2D:
Figure 2D:
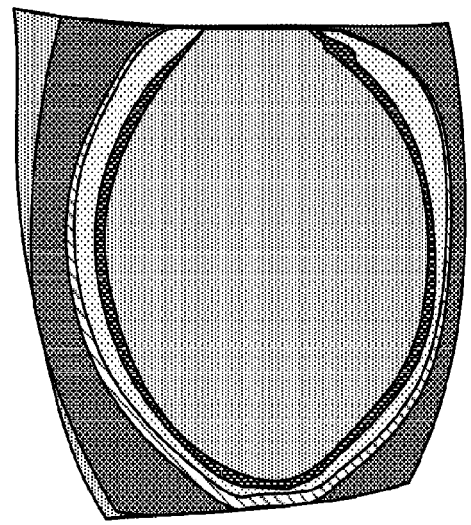

The 4D model may also include, as noted, myocardial electrical conductance properties, such as electrical conductivity of the left ventricular and right ventricular endocardial or bulk myocardial tissue in the muscle fiber and transverse orientations as well as conductivities in the infarcted or ischemic regions. The potentials may be described by a model of human ventricular myocytes modified to accommodate changes in channel kinetics occurring during heart failure. FIG. 2D depicts an example of the heart membrane potential. Action potential propagation may be modeled in a mono-domain or bi-domain reaction-diffusion mathematical framework. Electrical conductivity in the ventricular domain may be partitioned into left ventricle and right ventricle sub-endocardial regions (for example, ~3 mm transmurally adjacent to the ventricular cavities), infarct region, and the remaining bulk myocardium. The conductivity in the endocardial regions may be allowed to vary up to about for example 10 times that of bulk myocardium to account for the fast conduction of the Purkinje system, if not explicitly modeled. In infarcted or ischemic regions, conductivity may be isotropic, and the conductivity may be allowed to vary between about 10%-90% of that in the bulk myocardium.

To combine the 3D anatomic model of the heart (which is obtained from the image data 108) and the ECG data 105, the data processor may register (for example, align) the data so that the ECG data are aligned with the proper orientation(s) of the heart (or ventricle regions thereof). Moreover, although the previous example refers to ECG data, the data may comprise other types of electrical data including for example VCG data. Specifically, the coordinate axes of VCG data and/or the coordinate axes of the model are rotated until they are correctly aligned with each other.

To perform the registration, the ventricular myocardium from apex to the basal valve plane may be identified in, for example CT images 105, which may then be segmented and discretized. The coordinate frame of the resulting geometry may be rotated and aligned to coincide with the reference frame of the electrical data, such as the ECG or VCG data received at 105. For example, the positive x-direction may correspond to right to left (lead I); the positive y-direction may correspond to superior to inferior (lead aVF); the z-direction may correspond to anterior to posterior (~lead–V1).

As noted above, a simulated heart vector may be determined, at 113, from the 4D model of the patient's heart and electrical activity. The simulated heart vector may represent a simulated VCG or cardiac dipole. The simulated heart vector may represent the net intracellular current that flows from regions of higher intracellular potential to regions of lower potential at the depolarization and repolarization wave fronts at a given instant of time in the myocardium. The local activation time may be defined as the time at which the resting local intracellular potential depolarizes beyond some prescribed threshold value (for example, 0 mV) or achieves its maximal rate of change ($dV/dt_{max}$). The magnitude of the simulated heart vector may be proportional to the effective intracellular conductivity of the tissue and the strength of the potential gradients. The heart vector may have an orientation in the mean direction of the propagating wave front.

In some example embodiments, the simulated heart vector, $\Phi_H$ may be generated by a data processor in accordance with the following equation:

$$\Phi'_H = -\int_\Omega \sigma_i \nabla \Phi_i d\Omega \qquad \text{Equation 1,}$$

wherein $\sigma_i$ represents the intracellular conductivity, $\Phi_i$ represents the intracellular potential, and $\Omega$ represents the geometric domain of the ventricular myocardium.

There may also be a relationship between the derived heart vector 116 and body-surface electrocardiogram recordings (obtained at 105) which may be expressed as:

$$\Phi_H = A \cdot \Phi_B \qquad \text{Equation 2,}$$

wherein $\Phi_H$ is the derived heart vector 116, $\Phi_B$ is a vector of electrocardiogram recordings on the body surface (ECG), and A is the matrix of transfer coefficients accounting for the passive conductivity of the thoracic cavity tissue and fluids. Some example transformation coefficients, A, are given in Table 1, which are determined from Inverse Dower and Kors transformations. The heart vector $\Phi_H$ computed based on Equation 2 from clinical data 105 may be compared, as described further below, with the simulated heart vector $\Phi'_H$ computed based on Equation 1 from the model.

TABLE 1

| | Inverse Dower | | | | Kors | | |
|---|---|---|---|---|---|---|---|
| | X | Y | Z | | X | Y | Z |
| V1 | −0.17 | 0.06 | −0.23 | V1 | −0.13 | 0.06 | −0.43 |
| V2 | −0.07 | −0.02 | −0.31 | V2 | 0.05 | −0.02 | −0.06 |
| V3 | 0.12 | −0.11 | −0.25 | V3 | −0.01 | −0.05 | −0.14 |
| V4 | 0.23 | −0.02 | −0.06 | V4 | 0.14 | 0.06 | −0.2 |
| V5 | 0.24 | 0.04 | 0.06 | V5 | 0.06 | −0.17 | −0.11 |
| V6 | 0.19 | 0.05 | 0.11 | V6 | 0.54 | 0.13 | 0.31 |
| I | 0.16 | −0.23 | 0.02 | I | 0.38 | −0.07 | 0.11 |
| II | −0.01 | 0.89 | 0.10 | II | −0.07 | 0.93 | −0.23 |

Figure 3:
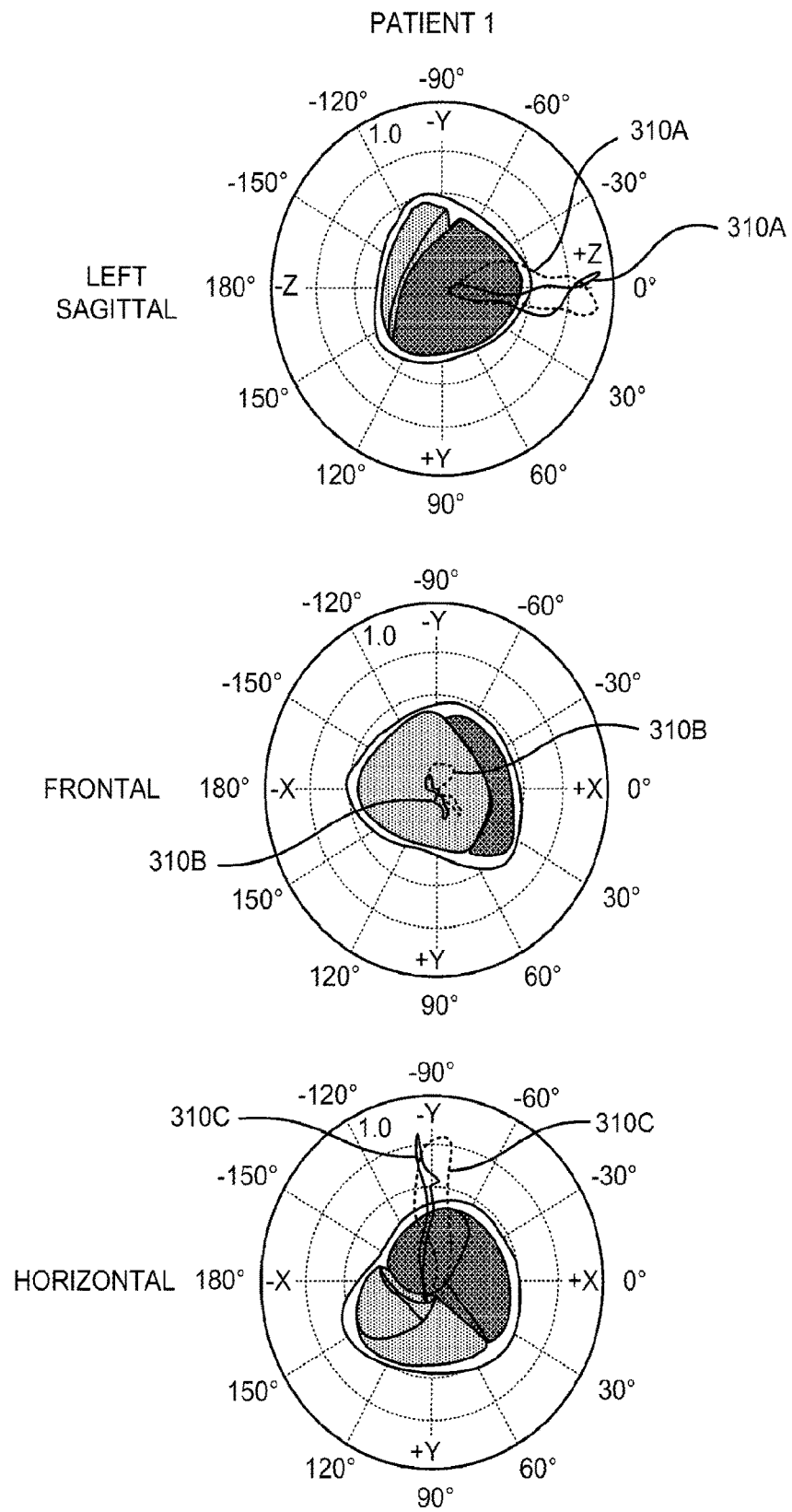
FIG. 3 depicts examples of loops formed by the tips of simulated heart vectors as the vectors change over the time period of a cardiac cycle, in accordance with some example embodiments.

FIG. 3 depicts for a patient the simulated heart vectors 310A-C (in blue) determined at 113 from the 4D model. The simulated heart vectors may be presented on a computer display to enable a health care provider to assess the simulated heart vector in order to visualize the magnitude and direction of electrical wave propagation in the heart and the sequences of regional electrical activation and repolarizations, which may reveal abnormal patterns of electrical activity indicative of certain cardiac disorders including bundle branch block. FIG. 3 also depicts, for the patient, the actual, measured VCGs 312A-C (in green) determined or derived at 116. The loops 310A-C/312A-C represent the spatial trajectory of the tip of the cardiac dipole with its tail at the origin. The polar plots show the projections of the simulated (blue) and measured (green) VCG loops (which may be based on Kors transformation, for example) on to the left sagittal, frontal, and horizontal planes. The relative orientation of the loops to the anatomical meshes (red—LV endocardial surface; blue—RV endocardial surface) is also illustrated.

Referring again to FIG. 1 at 120, the simulated heart vector $\Phi'_H$ may be compared with the patient's measured heart vector $\Phi_H$ (VCG) derived from body-surface electrocardiogram recordings 116. For example, a data processor may compare the simulated heart vector generated from the 4D model 110 with the measured patient's VCG 116. The patient's measured VCG may be measured directly or derived from the measured ECG data 105 as noted above.

In some example embodiments, the comparison may be based on an objective function, $\theta$. Specifically, the objective function, $\theta$, may be used to compare the orientations of the simulated heart vector and measured patient VCG. Based on this comparison, one or more of the parameters of the 4D model may be adjusted, at 130, to minimize the objective function or some alternative measure of the difference between the simulated heart vector and measured patient VCG.

The objective function is thus optimized so that the simulated heart vector best approximates in magnitude and direction of electrical propagation that estimated from the patient's measured VCG or ECG. The results of this optimization are parameters of the 4D model of heart electrical activity that may represent characteristics of the individual patient including their early activated ventricular site or sites and their myocardial electrical conductivities for the subendocardium, bulk myocardium and infarct tissue in the left and right ventricles along fiber and transverse axes. In some implementations, the objective function, $\theta$, may take the following form:

$$\theta = \frac{1}{t_{tot}} \sum_{t=1}^{t_{tot}} |\tilde{v}_t^m| \left( \frac{\mathrm{acos}\left(\frac{\tilde{v}_t^s \cdot \tilde{v}_t^m}{|\tilde{v}_R^s||\tilde{v}_R^m|}\right)}{\pi} \right), \quad \text{Equation 3}$$

wherein at time t, $\tilde{v}_t^m$ is the measured dipole, $\tilde{v}_t^s$ is the simulated dipole, $\tilde{v}_R^m$ is the measured dipole at the R peak, and $\tilde{v}_R^s$ is the simulated dipole at the R peak, and $t_{tot}$ is the total simulated activation time of the whole ventricle (for example, the number of time points during depolarization at which $\tilde{v}_t^s$ is computed) which is comparable to the measured QRS duration from the clinical electrocardiograms. The objective function, $\theta$, of Equation 3 may compute the weighted time-average of the dot products between the two dipoles, such as the simulated heart vector and measured patient VCG. In this example, the objective function, $\theta$, represents the maximal angle in the plane containing the two dipoles. Weighting by the relative strength of the measured signal may tend to favor deviations between the dipoles with greater magnitude.

The following provides an example for purposes of illustration. Electrophysiological parameters including a single ectopic stimulus site and electrical conductivity values may be adjusted to simulate an activation sequence with a simulated heart vector 113 that best matches the measured/derived VCG 116. Stimulus sites may be sampled at for example 118 locations (see Table 2 below) in the RV (right ventricle) endocardium spanning from apex to base and anterior to posterior septal junctions. Stimuli may be applied for a duration of 5 ms at a magnitude of 80,000 µA/cm³. Electrical conductivity in the sheet direction of the bulk myocardial regions ($\sigma_{bulk}$) may be sampled in the range of 0.0001 to 0.004 cm²/ms. Electrical conductivity ratios with respect to $\sigma_{bulk}$ in the LV ($\lambda_{LV}$) and RV ($\lambda_{RV}$) subendocardial regions may be sampled in the range of about 1 (myocardial conduction) and about 10 (fast Purkinje conduction). Possible parameter combinations may be created for each patient and stored as a computational model 110.

TABLE 2

| Stimulus locations | $\sigma_{bulk}$ (cm²/ms) | $\lambda_{LV}$, $\lambda_{RV}$ | $\lambda_{scar}$ |
|---|---|---|---|
| 118 | 1e–4–4e–3 | 1–10 | 0.1–0.9 |

Referring again to FIG. 1, if the simulated heart vector 113 and measured patient VCG 116 are sufficiently similar, based on the objective function ($\theta$), the 4D model 110 may be considered complete or ready (no adjustment at 130), in which case the output parameters 142-149 from the 4D model 110 may be output at 140.

If however the simulated heart vector 113 and measured patient VCG 116 are not sufficiently similar based on the objective function ($\theta$), one or more parameters of the 4D model 110 may be adjusted (yes at 130), in which case a new simulated heart vector 113 is determined and another comparison is performed at 120. The adjustment of the 4D model may include adjusting, at 130, one or more of the following parameters of the 4D model 110 of the patient's electrical activity: the location of the early stimulus site and conductivity tensor components in different parts of the ventricle including the left ventricle wall, right ventricle wall, non-infarcted myocardium, and infarcted myocardium.

The 4D model 110 may provide an output 140 which may include parameters 142-149, which can be obtained directly, or derived, from the 4D model 110.

The model output parameters 140 may include one or more ectopic early stimulus sites 142 that produce an electrical activation pattern that approximates, such as a best approximation for example that is estimated by a patient's measured VCG. Alternatively or additionally, output 140 may include the right and/or left ventricle wall conductivity 144. Alternatively or additionally, output 140 may include an indication of how readily the activation propagates 148 through the myocardium. This propagation speed indicator 144 represents the trajectory and speed of the activation from the origin. Alternatively or additionally, output 140 may include the 3D ventricular activation patterns 149 estimated from the 4D model.

In some example embodiments, the parameters 142-148 may be used to determine a dyssynchrony metric 150 (which is determined from the model), in accordance with some example embodiments. The dyssynchrony metric 150 may be calculated from 3D electrical activation pattern 149 estimated by the 4D model from the combination of one or more of the output parameters 142-148, as well as other parameters obtained from the 4D model such as for example the parameters disclosed herein at Tables 2 and 3 for example.

The dyssynchrony metric 150 may provide an indication 152 of whether cardiac resynchronization therapy (CRT) may be a useful treatment for dyssynchronous heart failure, bundle branch block (BBB), and/or other cardiac conditions. Moreover, the dyssynchrony metric 150 may be used provide a treatment configuration 154, such as where and/or how to apply the cardiac resynchronization therapy. The dyssynchrony metric may indicate the degree to which a particular CRT pacing protocol reduces the left ventricular activation delay or a similar measure of dyssychrony which may lead to optimal long-term therapeutic outcomes. Predictive metrics, such as the delay between earliest septal and latest left ventricular activation times, cannot be determined directly from the ECG or VCG. However, these predictive metrics can be determined from the 4D model 110.

In some example embodiments, process 100 may thus provide a patient specific computational model of the heart, such as 4D model 110, that is generated from patient electrical data such as 12-lead ECG data 105 and further generated from image data 108, such as patient biventricular cardiac geometry data obtained from a cardiac imaging as well as other types of data.

In some example embodiments, the 4D model 110 may provide estimates of ventricular activation sites and myocardial conductivities. From these estimates, a data processor may predict three-dimensional sequences of electrical depolarization in the ventricular walls of patients with (left or right, complete or incomplete) bundle branch block.

In some example embodiments, a transmembrane current model (which includes calcium kinetic(s)) may be used to provide an extension of the 4D model 110 to ventricular repolarization and/or electromechanics.

In some example embodiments, the 4D heart model 110 (for patients with complete or incomplete, left or right bundle branch block) may, as noted, include one or more parameters, and the set of parameters (which can be selected after the adjustment is complete at 130) and then output at 140-154 for example may represent a solution set of parameters (solution parameters). These parameters and, in particular, the solution parameters may correlate strongly with, and predict the, long-term outcome of cardiac resynchronization therapy (CRT) for dyssynchronous heart failure patients. For example, the computational model 110 may produce a set of regional myocardial activation times or patterns, from which a feature vector of parameters may be obtained. These parameters may include measures of the electrical dyssynchrony in the left ventricle at baseline prior to cardiac resynchronization therapy. When the 4D model is used to obtain baseline parameters before cardiac resynchronization therapy, the baseline solutions (which may be used to compute dyssynchrony metric 150, parameters 142-148 and/or other patient-specific parameters, variables, or metrics) may strongly predict the long-term outcome of cardiac resynchronization therapy (as measured by a decrease in left ventricular end-systolic volume or an increase in ejection fraction or some other quantitative long-term improvement in cardiac function or reverse heart failure remodeling) at a given time after cardiac resynchronization therapy, such as 3-6 months after cardiac resynchronization therapy initiation. These parameters may also include the change in electrical dyssynchrony that may be induced by cardiac resynchronization therapy, and this change may also predict the outcome of cardiac resynchronization therapy at a later time, such as 3-6 months after cardiac resynchronization therapy.

In some example embodiments, the cardiac resynchronization therapy parameters may be included in, or determined from, the dyssynchrony metrics computed from the regional 3D ventricular electrical activation times 149 estimated by the 4D model 110 that best matches the clinical data 105. Examples of the dyssynchrony metrics include: (1) the total activation duration in the whole left ventricle; (2) the total activation duration between the earliest activation time in the septum and the latest activation in the whole left ventricle; (3) the delay between the mean activation times in the septum and left ventricular lateral walls; (4) the difference in total activation time between the septal and right ventricular walls; (5) the delay between the earliest activation times in the septum and right ventricle; (6) the delay between the earliest activation times in the whole left ventricle and the right ventricle; (7) the difference in total activation time between left ventricular and right ventricular walls; (8) the delay between the earliest activation times in the left and right ventricles; (9) the difference in total activation time between the left ventricular lateral and right ventricular walls; and/or (10) the delay between the earliest activation times in the left ventricular lateral wall and the right ventricle. Table 3 provides a summary of these parameters.

TABLE 3

| Metric Title | Description | Equation |
| --- | --- | --- |
| Total LV AT duration (% QRS) | The total activation duration in the whole LV. The $AT_{LV\_max}$ is the latest activation time in the LV, and the parameter $AT_{LV\_min}$ is the earliest activation time in the LV. $QRS_{LBBB}$ is the measured QRS duration during LBBB. | $\dfrac{AT_{LV\_max} - AT_{Lv\_min}}{QRS_{LBBB}}$ |
| Late LV-early ST duration (% QRS) | The total activation duration between the earliest activation time in the septum and the latest activation in the whole LV. This is similar to metric (1) in some respects. $AT_{ST\_min}$ is the earliest activation time of the interventricular septum. | $\dfrac{AT_{LV\_max} - AT_{ST\_min}}{QRS_{LBBB}}$ |
| Mean LVlat-ST AT difference | The delay between the mean activation times in the septum and LV lateral wall. $AT_{LVlat\_mean}$ is the mean activation time of the LV lateral wall. $AT_{ST\_mean}$ is the mean | $\dfrac{AT_{LVlat\_mean} - AT_{ST\_mean}}{QRS_{LBBB}}$ |

TABLE 3-continued

| Metric Title | Description | Equation |
|---|---|---|
| ST-RV AT duration difference | activation time of the interventricular septum. The difference in total activation time between ST and RV regions. The parameter $AT_{STmax}$ is the latest activation time of the interventricular septum. $AT_{RV\_max}$ is the latest activation time in the RV. $AT_{RV\_min}$ is the earliest activation time in the RV. | $\dfrac{(AT_{ST\_max} - AT_{ST\_min})}{AT_{STmax}} - \dfrac{(AT_{RV\_max} - AT_{RV\_min})}{AT_{RV\_max}}$ |
| ST-RV early AT delay (% QRS) | The delay between the earliest activation times in the septum and RV. | $\dfrac{AT_{ST\_min} - AT_{RV\_min}}{QRS_{LBBB}}$ |
| LV-RV electrical early AT delay (% QRS) | The delay between the earliest activation times in the whole LV and RV. | $\dfrac{AT_{LV\_min} - AT_{RV\_min}}{QRS_{LBBB}}$ |
| LV-RV AT duration difference | The difference in total activation time between LV and RV regions. | $\dfrac{(AT_{LVlat\_max} - AT_{LVlat\_min})}{AT_{LVlat\_max}} - \dfrac{(AT_{RV\_max} - AT_{RV\_min})}{AT_{RV\_max}}$ |
| LV-RV early AT delay (% QRS) | The delay between the earliest activation times in the LV and RV. | $\dfrac{AT_{LV\_min} - AT_{RV\_min}}{QRS_{LBBB}}$ |
| LV lateral-RV AT duration difference (% max ATs) | The difference in total activation time between LV lateral and RV regions. $AT_{LVlat\_max}$ is the latest activation time in the LV lateral wall. $AT_{LVlat\_min}$ is the earliest activation time in the LV lateral wall. | $\dfrac{(AT_{LVlat\_max} - AT_{LVlat\_min})}{AT_{LVlat\_max}} - \dfrac{(AT_{ST\_max} - AT_{ST\_min})}{AT_{ST\_max}}$ |
| LV lateral-RV electrical early AT delay (% QRS) | The delay between the earliest activation times in the LV lateral wall and RV. | $\dfrac{AT_{LVlat\_min} - AT_{ST\_min}}{QRS_{LBBB}}$ |

Figure 4:
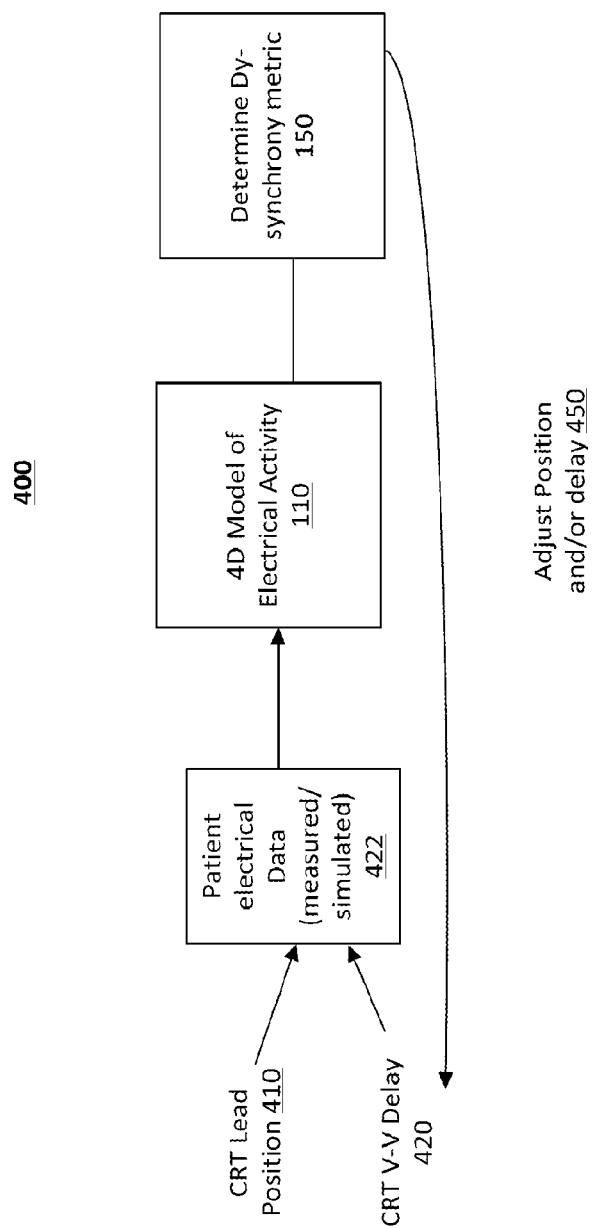
FIG. 4 depicts an example process for cardiac resynchronization therapy treatment using the computational model, in accordance with some example embodiments.

FIG. 4 depicts an example process 400 for determining parameters for use in cardiac resynchronization therapy treatment of a patient.

Quantities obtained, or determined from, the 4D model 110 may be used to determine cardiac resynchronization therapy, including cardiac resynchronization therapy lead placement and cardiac resynchronization therapy pacing protocols. For example, the patient-specific model 110 may be used to find the cardiac resynchronization therapy pacing parameters, such as lead positions and V-V delay, that minimize the dyssynchrony as defined by one or more of the parameters or dyssynchrony metric described above. The parameters or dyssynchrony metric described above may be used to place a cardiac resynchronization therapy lead at, or near, the latest activated site(s) on the ventricular walls or at a location predicted by the model to achieve reduction in dyssynchrony that may be optimal for therapeutic outcomes. Optimal deployment of multi-site pacing electrodes may also be found in this way. In some patients with left bundle branch block, this method may predict optimal therapeutic outcomes that can be achieved with a negative V-V delay (i.e., earliest pacing at the right ventricular lead). The change in one or more of the quantities described above determined in patients in the same manner after therapy can provide a way to assess the outcome or effectiveness of cardiac resynchronization therapy. The electrical dyssynchrony metric computed from the patient-specific model 110 may thus provide: (1) improved clinical assessment of the severity of electrical dyssynchrony and dyssynchronous heart failure; (2) assessment of therapeutic efficacy at follow-up; and/or (3) determination of therapeutic parameters that optimize outcomes by minimizing dyssynchrony.

Once the 4D model 110 is generated, the model 110 may be used to assess cardiac resynchronization therapy treatment as noted above. The process 400 may be used to choose an optimal V-V delay for cardiac resynchronization therapy that minimizes one or more of the dyssynchrony metric or parameters disclosed herein. For example, a patient undergoing cardiac resynchronization therapy treatment may be treated with a cardiac resynchronization therapy treatment configuration including CRT lead positions 410 and V-V delay 420. The electrical data measured (or simulated) 422 from this treatment may then be provided as an input to the 4D model 110. The output parameters from the model 110 may be used directly or used to compute a metric, such as the dyssynchrony metric 150. From the parameters and/or dyssynchrony metric, the likelihood that the cardiac resynchronization therapy treatment will be effective given the treatment configuration can be assessed. Moreover, the cardiac resynchronization therapy treatment configuration may be adjusted at 450, and the processes 400 repeated to determine whether the adjusted cardiac resynchronization therapy treatment configuration offers an improvement when compared with the initial cardiac resynchronization therapy treatment configuration.

In some example embodiments, the dyssynchrony metric 150 and/or parameters disclosed herein determined from patient-specific model 110 may also be used to train machine learning algorithms. When this is the case, machine learning may discover dyssynchrony metrics of dyssynchrony directly from patient VCG that predict cardiac resynchronization therapy outcome. For example, the computational model may be general to a plurality of patients, and used for a plurality of patients.

Moreover, solution(s) of the 4D model may include a distribution in space and time of transmembrane potentials (Vm) during the cardiac cycle throughout the anatomical model. Thus, the activation times can be obtained from the solution for some, if not all, regions of the heart (or ventricular) walls.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other. For example, a computer may be used to perform one or more aspects of process 100 and/or 400, such as receive three-dimensional image data representative of a heart; receive electrical data representative of electrophysiology of the heart; generate, based on the received three-dimensional image data and the received electrical data, a computational model of the heart; generate a simulated heart vector; compare, based on an objective function, the simulated heart vector to patient VCG data; perform model adjustments; provide outputs such as parameters or the dyssynchrony metric; generate user interfaces or views for presentation; and/or perform other operations disclosed herein.

In some example embodiments, one or more aspects of processes 100, 400, and/or the like disclosed herein may be included in a pacemaker/defibrillator pulse generator and/or the interrogator for transmitting data to, and receiving data from, the pulse generator. For example, the pacemaker may include processor circuitry and memory, wherein the memory includes computer program code for executing one or more aspects of processes 100, 400, and/or the like disclosed herein to vary pacing parameters.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed:

1. A method comprising:
   receiving three-dimensional image data representative of a heart of a patient;
   receiving electrical data representative of an electrophysiology of the heart;
   generating a computational model of the heart by at least combining the received three-dimensional image data and the received electrical data, the computational model of the heart providing time-varying electrical dynamics of the heart;
   determining, based at least on the computational model of the heart, a dyssynchrony metric predictive of a responsiveness of the patient to a cardiac pacing therapy; and
   administering, based at least on the dyssynchrony metric, the cardiac pacing therapy, the dyssynchrony metric determining one or more lead placements and/or an interventricular stimulation delay for the administering of the cardiac pacing therapy.

2. The method of claim 1, further comprising:
   determining, from the computational model of the heart, a simulated heart vector.

3. The method of claim 2, wherein the simulated heart vector predicts a vectorcardiogram of a patient.

4. The method of claim 3, further comprising:
   adjusting the simulated heart vector based on a comparison of the simulated heart vector to the vectorcardiogram, the vectorcardiogram being estimated using a 12-lead electrocardiogram obtained from the patient.

5. The method of claim 4, wherein the comparison is based on optimizing an objective function.

6. The method of claim 1, wherein the electrical data comprises time varying electrocardiogram data.

7. The method of claim 1, wherein the three-dimensional image data comprises at least one of an echocardiograph, a computed tomograph, a myocardial perfusion scan, or a magnetic resonance image set.

8. The method of claim 1, wherein the three-dimensional image data and the electrical data are combined by at least:

generating, based at least on the three-dimensional image data, a finite element mesh of the heart including a left ventricle of the heart and/or a right ventricle of the heart; and aligning a location associated with the electrical data to the same location in the generated finite element mesh.

9. The method of claim 1, further comprising:

determining, based at least on the computational model of the heart, an origin of the electrical activation, a conductivity of a myocardial tissue, and/or a speed at which the activation traverses a myocardium of the heart.

10. The method of claim 1, wherein the dyssynchrony metric includes at least one of a first total activation duration in an entire left ventricle, a second total activation duration between an earliest activation time in a septum and a latest activation in the entire left ventricle, a first delay between mean activation times in the septum and a portion of a left ventricular lateral wall; a first difference in total activation times between the septum and a portion of a right ventricular wall, a second delay between the earliest activation times in the septum and a right ventricle, a second delay between the earliest activation times in the entire left ventricle and the right ventricle, a second difference in total activation times between left ventricular and right ventricular walls, a third delay between earliest activation times in left and right ventricles, a second difference in total activation times between a left ventricular lateral wall and a right ventricular wall, and/or a fourth delay between earliest activation times in the left ventricular lateral wall and the right ventricle.

11. The method of claim 1, further comprising:

generating, for presentation on a display, a user interface including a representation of the computational model of the heart and at least one of the dyssynchrony metric, the origin of the electrical activation, the conductivity of the myocardial tissue, and the speed at which the activation traverses the myocardium.

12. The method of claim 1, wherein the computational model comprises a four dimensional model of the heart.

13. The method of claim 1, wherein the computational model of the heart represents a net intracellular current flowing from a first region of higher intracellular potential to a second region of lower intracellular potential at a given time within a myocardium of the heart, and wherein the net intracellular current flow occurs at a depolarization wave front and/or a repolarization wave front.

14. An apparatus comprising:

at least one processor; and at least one memory including computer program code, the at least one memory and the computer program code configured to, with the at least one processor, cause the apparatus to perform at least the following:

receive three-dimensional image data representative of a heart of a patient;

receive electrical data representative of an electrophysiology of the heart;

generate a computational model of the heart by at least combining the received three-dimensional image data and the received electrical data, the computational model of the heart providing time-varying electrical dynamics of the heart;

determine, based at least on the computational model of the heart, a dyssynchrony metric predictive of a responsiveness of the patient to a cardiac pacing therapy; and administer, based at least on the dyssynchrony metric, the cardiac pacing therapy, the dyssynchrony metric determining one or more lead placements and/or an interventricular stimulation delay for the administration of the cardiac pacing therapy.

15. The apparatus of claim 14, wherein the electrical data comprises time varying electrocardiogram data.

16. The apparatus of claim 14, wherein the three-dimensional image data comprises at least one of an echocardiograph, a computed tomograph, a myocardial perfusion scan, or a magnetic resonance image set.

17. The apparatus of claim 14, wherein the three-dimensional image data and the electrical data are combined by at least:

generating, based at least on the three-dimensional image data, a finite element mesh of the heart including a left ventricle of the heart and/or a right ventricle of the heart; and aligning a location associated with the electrical data to the same location in the generated finite element mesh.

* * * * *